(12) United States Patent
Giles et al.

(10) Patent No.: US 11,395,759 B2
(45) Date of Patent: Jul. 26, 2022

(54) METHOD AND APPARATUS PERTAINING TO SECUREMENT OF A PERSONAL PATIENT WARMING APPARATUS

(71) Applicant: Medline Industries, LP, Northfield, IL (US)

(72) Inventors: Andrew Giles, Libertyville, IL (US); Robert Lockwood, Libertyville, IL (US)

(73) Assignee: Medline Industries, LP, Northfield, IL (US)

( * ) Notice: Subject to any disclaimer, the term of this patent is extended or adjusted under 35 U.S.C. 154(b) by 547 days.

(21) Appl. No.: 14/462,094

(22) Filed: Aug. 18, 2014

(65) Prior Publication Data

US 2016/0045362 A1 Feb. 18, 2016

(51) Int. Cl.
*A61F 7/00* (2006.01)
*A47G 9/02* (2006.01)

(52) U.S. Cl.
CPC ...... *A61F 7/0097* (2013.01); *A61F 2007/006* (2013.01); *A61F 2007/0091* (2013.01); *A61F 2007/0098* (2013.01)

(58) Field of Classification Search
CPC .............. A61F 7/0097; A61F 2007/006; A61F 2007/0091
See application file for complete search history.

(56) References Cited

U.S. PATENT DOCUMENTS

| 17,102 A | 4/1857 | Lefebure |
|---|---|---|
| 1,777,982 A | 10/1930 | Popp |
| 2,311,899 A | 2/1943 | Marlowe |
| 3,444,922 A | 5/1969 | Dingman |
| 3,610,251 A | 10/1971 | Sanderson |
| 4,572,188 A | 2/1986 | Augustine |
| 4,867,230 A | 9/1989 | Voss |
| 5,165,127 A | 11/1992 | Nicholson |
| 5,184,612 A | 2/1993 | Augustine |
| 5,265,599 A | 11/1993 | Stephenson |
| 5,300,098 A | 4/1994 | Philipot |
| 5,300,100 A | 4/1994 | Hickle |
| 5,300,102 A | 4/1994 | Augustine |
| 5,324,320 A | 6/1994 | Augustine |
| 5,336,250 A | 8/1994 | Augustine |
| 5,343,579 A | 9/1994 | Dickerhoff |
| 5,383,918 A | 1/1995 | Panetta |
| 5,384,924 A | 1/1995 | Dickerhoff |

(Continued)

*Primary Examiner* — Tigist S Demie
(74) *Attorney, Agent, or Firm* — Fitch, Even, Tabin & Flannery LLP

(57) ABSTRACT

A personal patient warming apparatus includes a blanket having at least one pneumatic pathway formed therethrough and a plurality of orifices formed through at least one side thereof through which warmed air can exit to warm a patient. The blanket further includes a first portion configured to cover a first appendage of the patient when the blanket is disposed over the patient and a second portion configured to cover a second appendage of the patient when the blanket is disposed over the patient. Both the first portion and the second portion each include at least one tear line configured to form, when torn, an opening in the blanket through which at least one of the patient's appendages and an operating room table appendage board is disposed when disposing the blanket over the patient.

9 Claims, 7 Drawing Sheets

(56) References Cited

U.S. PATENT DOCUMENTS

| | | | |
|---|---|---|---|
| 5,392,847 A | 2/1995 | Stephenson | |
| 5,405,370 A | 4/1995 | Irani | |
| 5,405,371 A | 4/1995 | Augustine | |
| 5,514,169 A | 5/1996 | Dickerhoff | |
| 5,522,871 A | 6/1996 | Sternlicht | |
| 5,588,968 A | 12/1996 | Sternlicht | |
| 5,620,482 A | 4/1997 | Augustine | |
| 5,632,769 A | 5/1997 | Kappel | |
| 5,643,337 A | 7/1997 | Kappel | |
| 5,658,325 A | 8/1997 | Augustine | |
| 5,672,188 A | 9/1997 | Choi | |
| 5,674,269 A | 10/1997 | Augustine | |
| 5,675,848 A | 10/1997 | Kappel | |
| 5,716,387 A | 2/1998 | Kappel | |
| 5,735,890 A | 4/1998 | Kappel | |
| 5,749,109 A | 5/1998 | Kappel | |
| 5,773,275 A | 6/1998 | Anderson | |
| 5,792,216 A | 8/1998 | Kappel | |
| 5,824,025 A | 10/1998 | Augustine | |
| 5,839,133 A | 11/1998 | Dickerhoff | |
| 5,890,243 A * | 4/1999 | Dickerhoff | A47G 9/0215 5/423 |
| 5,928,274 A | 7/1999 | Augustine | |
| 5,968,084 A | 10/1999 | Augustine | |
| 5,974,605 A | 11/1999 | Dickerhoff | |
| 6,126,393 A | 10/2000 | Arnold | |
| 6,156,058 A | 12/2000 | Kappel | |
| 6,168,612 B1 | 1/2001 | Augustine | |
| 6,176,870 B1 | 1/2001 | Augustine | |
| 6,203,567 B1 | 3/2001 | Augustine | |
| 6,210,428 B1 | 4/2001 | Augustine | |
| 6,241,756 B1 | 6/2001 | Kappel | |
| 6,277,144 B1 | 8/2001 | Tomic-Edgar | |
| 6,290,716 B1 | 9/2001 | Augustine | |
| 6,309,409 B1 | 10/2001 | Anderson | |
| 6,440,157 B1 | 8/2002 | Shigezawa | |
| 6,487,871 B1 | 12/2002 | Augustine | |
| 6,511,501 B1 | 1/2003 | Augustine | |
| 6,524,332 B1 | 2/2003 | Augustine | |
| 6,530,976 B2 | 3/2003 | Murai | |
| 6,544,283 B2 | 4/2003 | Augustine | |
| RE38,462 E | 3/2004 | Augustine | |
| 6,699,270 B2 | 3/2004 | Gammons | |
| 6,709,447 B1 | 3/2004 | Gammons | |
| 6,800,087 B2 | 10/2004 | Papay | |
| 6,827,729 B2 | 12/2004 | Gammons | |
| 6,876,884 B2 | 4/2005 | Hansen | |
| 7,001,416 B2 | 2/2006 | Augustine | |
| 7,014,431 B2 | 3/2006 | Hansen | |
| 7,037,068 B2 | 5/2006 | Cobb | |
| 7,041,122 B2 | 5/2006 | Paolini | |
| 7,066,949 B2 | 6/2006 | Gammons | |
| 7,101,389 B1 | 9/2006 | Augustine | |
| 7,276,076 B2 | 10/2007 | Bieberich | |
| 7,338,515 B2 | 3/2008 | VanDuren | |
| 7,470,280 B2 | 12/2008 | Bieberich | |
| 7,497,870 B2 | 3/2009 | Frey | |
| 7,517,360 B2 | 4/2009 | Frey | |
| 7,550,000 B2 | 6/2009 | Frey | |
| 7,572,285 B2 | 8/2009 | Frey | |
| 7,578,837 B2 | 8/2009 | Arnold | |
| 7,658,756 B2 | 2/2010 | Pierre | |
| 7,666,214 B2 | 2/2010 | Pierre | |
| 7,749,261 B2 | 7/2010 | Hansen | |
| 7,819,911 B2 * | 10/2010 | Anderson | A61F 7/00 607/107 |
| 7,837,721 B2 | 11/2010 | Augustine | |
| 7,846,192 B2 | 12/2010 | Panser | |
| 7,857,841 B2 | 12/2010 | Anderson | |
| 7,862,599 B2 | 1/2011 | Anderson | |
| 7,871,428 B2 | 1/2011 | Augustine | |
| 7,879,078 B2 | 2/2011 | Vardanega | |
| 7,901,443 B2 | 3/2011 | Vardanega | |
| 7,905,911 B2 | 3/2011 | Vardanega | |
| 7,914,566 B2 | 3/2011 | Anderson | |
| 7,951,184 B2 | 5/2011 | Schuessler | |
| 7,976,572 B2 | 7/2011 | Ziaimehr | |
| 8,002,940 B2 | 8/2011 | Pierre | |
| 8,048,137 B2 | 11/2011 | Pierre | |
| 8,105,370 B2 | 1/2012 | Augustine | |
| 8,167,922 B2 | 5/2012 | Ko | |
| 8,257,415 B2 | 9/2012 | Panser | |
| 8,308,785 B2 | 11/2012 | Pierre | |
| 8,317,849 B2 | 11/2012 | Pierre | |
| 8,328,859 B2 | 12/2012 | Hansen | |
| 8,470,011 B2 | 6/2013 | Ziaimehr | |
| 8,535,362 B2 | 9/2013 | VanLiebergen | |
| 8,608,788 B2 | 12/2013 | Starr | |
| 2006/0142825 A1 | 6/2006 | Dunlop | |
| 2008/0077207 A1 * | 3/2008 | Vardanega | A61F 7/0097 607/107 |
| 2008/0113608 A1 | 5/2008 | VanDuren | |
| 2009/0143844 A1 | 6/2009 | Cazzini | |
| 2010/0179624 A1 * | 7/2010 | Anderson | A61F 7/00 607/104 |
| 2010/0198321 A1 | 8/2010 | Moeck | |
| 2011/0098794 A1 * | 4/2011 | Anderson | A61F 7/0097 607/104 |
| 2011/0137387 A1 | 6/2011 | Vardanega | |
| 2012/0209360 A1 | 8/2012 | Dunlop | |
| 2013/0041438 A1 | 2/2013 | Loushin | |
| 2014/0257442 A1 * | 9/2014 | Ellingboe | A61F 7/0097 607/107 |

* cited by examiner

METHOD AND APPARATUS PERTAINING TO SECUREMENT OF A PERSONAL PATIENT WARMING APPARATUS

TECHNICAL FIELD

These teachings relate generally to personal patient warming systems.

BACKGROUND

Personal patient warming apparatuses are known in the art. Being "personal," these apparatuses do not serve in any meaningful way to warm a general area (such as a room). Instead, these apparatuses serve to provide local-to-a-patient warming for the benefit of an individual patient (typically during the administration of a medical-services procedure such as but not limited to an operation). While some of the delivered warmth will typically escape beyond the patient themselves, the focus of the warmth delivery mechanism is intended and designed to primarily warm the patient as versus the local environment.

One category of personal patient warming apparatus serves to deliver warmed air to the patient. By one common approach, the personal patient warming apparatus includes a blanket that overlies the patient. This blanket includes one or more internal pneumatic chambers/pathways. A blower forces warmed air into the blanket and that warmed air then exits the blanket via a plurality of small orifices (typically located on an underside surface of the blanket). The exiting warmed air, in turn, provides local warming in very close proximity to the patient.

Generally speaking, it is helpful if such a blanket stay more or less where placed on the patient by the medical technician until use of the blanket concludes. Since these blankets are typically comprised of very light materials, however, such a blanket can be easily dislodged during use. Furthermore, the warmed air escaping from the aforementioned orifices can serve in some cases to cause the blanket to move or to at least make such movement more likely to occur. To help control such movement, prior art blankets often provide one or more ties by which the blanket can be at least loosely secured in place. Though often satisfactory in practice to achieve the desired result, such ties do not necessarily meet the needs or requirements of all application settings and/or users.

BRIEF DESCRIPTION OF THE DRAWINGS

The above needs are at least partially met through provision of the method and apparatus pertaining to securement of a personal patient warming apparatus described in the following detailed description, particularly when studied in conjunction with the drawings, wherein.

Figure 1:
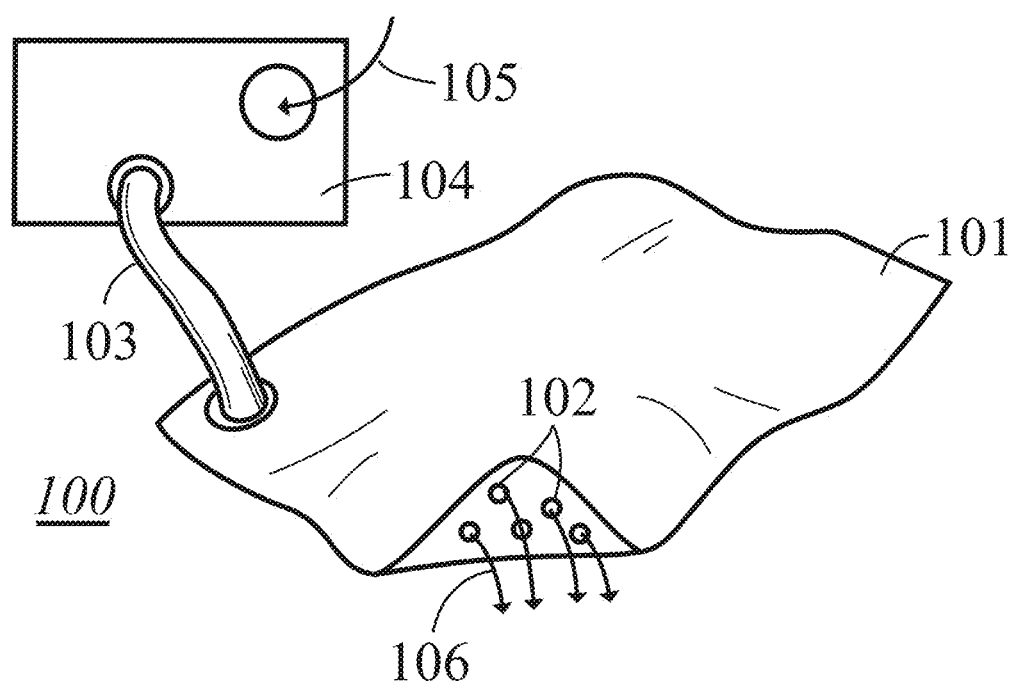
FIG. 1 comprises a schematic perspective view as configured in accordance with the prior art.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/ or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a personal patient warming apparatus includes a blanket having at least one pneumatic pathway formed therethrough and a plurality of orifices formed through at least one side thereof such that at least some warmed air that is introduced into the at least one pneumatic pathway will exit via the plurality of orifices to thereby warm a patient over whom the blanket is disposed. The blanket further includes a first portion configured to cover a first appendage of the patient when the blanket is disposed over the patient and a second portion configured to cover a second appendage of the patient when the blanket is disposed over the patient. Both the first portion and the second portion each include at least one tear line configured to form, when torn, an opening in the blanket through which at least one of the patient's appendages and an operating room table appendage board is disposed when disposing the blanket over the patient.

These teachings are highly flexible in practice and will accommodate a variety of modifications with respect to the foregoing. By one approach, for example, the aforementioned tear lines can comprise either or both of a line of perforations and a score line.

By one approach, each of the aforementioned portions of the blanket includes a first tear line that is aligned at least substantially parallel to the corresponding portion and wherein there is one or more additional tear lines that intersect with a corresponding one of the first tear lines. If desired, there are at least two such intersecting tear lines that are disposed at least substantially parallel to one another. So configured, a hole of sufficient size to accommodate the aforementioned appendage/operating room table's appendage board is easily and reliably made at the intersection of the first tear line with one of these additional tear lines.

So configured, a hole of a suitable size and at a location suitable to accommodate the dimensions of the patient and/or operating room table's appendage board is easily, reliably, and intuitively formed at a time of need. Forming the hole and disposing the corresponding appendage and/or operating room table's appendage board therethrough to securely maintain the blanket in an initially-placed position can be done quickly and with little or no training. For at least many medical services technicians this approach to securing the blanket is both easier and faster than using ties to secure the blanket.

Those skilled in the art will further appreciate that these teachings effectively leverage already-available materials (i.e., the blanket itself) and are therefore highly economical in practice.

These and other benefits may become clearer upon making a thorough review and study of the following detailed description. Referring now to the drawings, and in particular to FIG. 1, it may be helpful to first briefly recount a simple illustrative example of a personal patient warming apparatus 100 that delivers warmed air to a patient. In this example, the personal patient warming apparatus 100 includes a pneumatic blanket 101 having one or more pneumatic chambers formed therein and a plurality of small orifices 102 formed through the blanket material by which warmed air can escape from the aforementioned chamber(s).

A warm air delivery tube 103 couples the blanket's pneumatic chamber(s) to a heater/blower 104. The heater/blower 104 pulls in ambient air 105 through one or more intake ports using one or more fans or other air-moving mechanisms, warms that air using a heating methodology of choice, and pushes that warmed air out to the blanket 101 via the warm air delivery tube 103. That warmed air 106 then eventually exits the blanket 101 via the aforementioned orifices 102. When the blanket 101 overlies a patient that exiting warmed air 106 serves to provide localized warming for the patient.

Those skilled in the art will recognize that the prior art accommodates a wide number of variations as regards the foregoing. The specific construction and form factor of the blanket 101, for example, can vary considerably from one embodiment to another. As another example, there are all manner of approaches to heating the air and causing the air to move that are available for consideration. As the present teachings are not particularly sensitive to any particular selections in these regards, however, for the sake of brevity further elaboration in these regards will not be provided here aside from noting that the expression "personal patient warming apparatus" as used herein will be understood to include both the embodiment illustrated in FIG. 1 and other such variations as are reasonably associated therewith.

Figure 2:
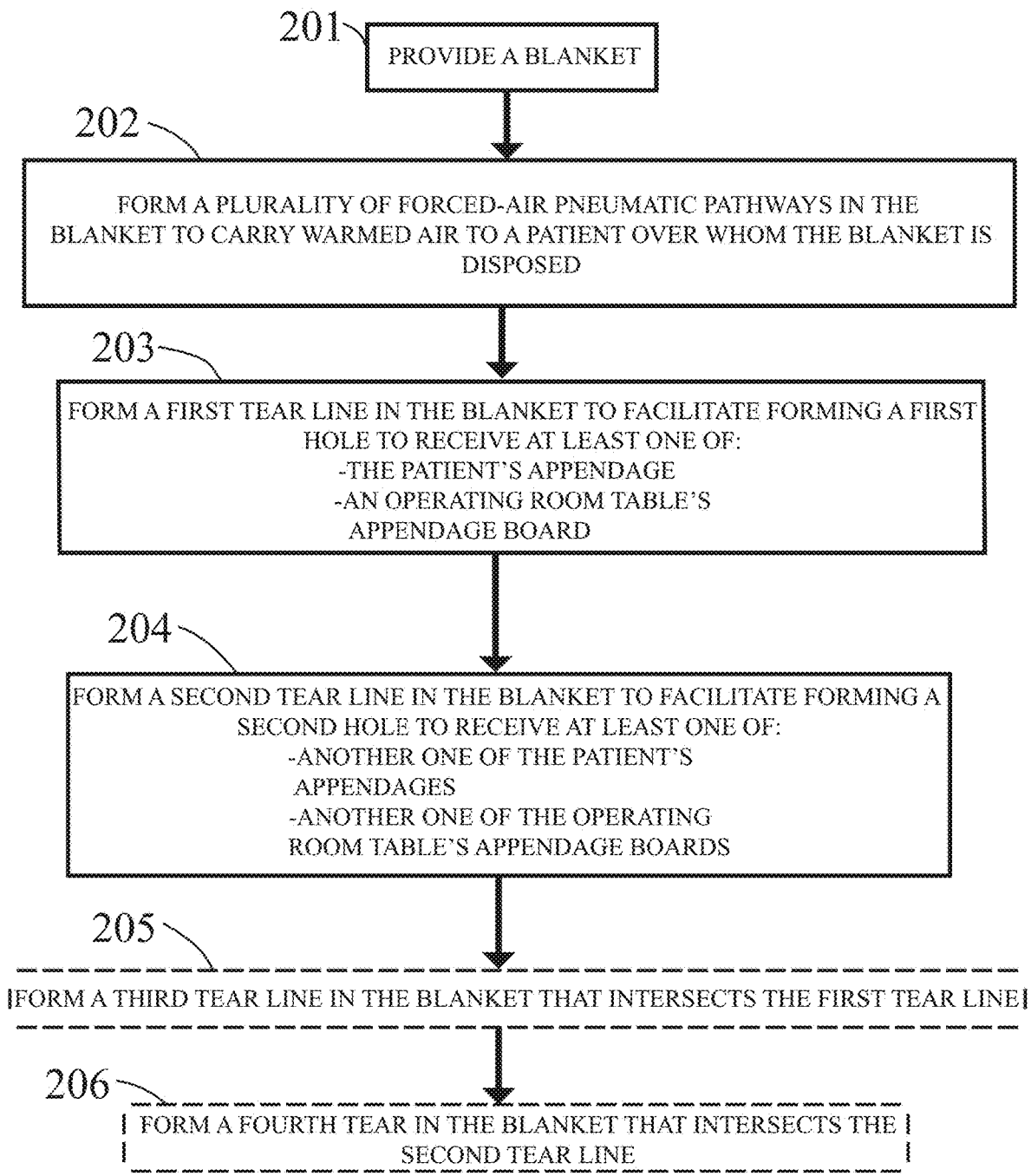
FIG. 2 comprises a flow diagram as configured in accordance with various embodiments of these teachings.

FIG. 2 illustrates a process 200 that comports with many of these teachings. At block 201 this process 200 provides a blanket 101 as generally described above. By one approach, and for the purposes of the present illustrative description, this blanket 101 comprises a one-time-use disposable blanket formed, for example, of lightweight plastic film. Per block 202 this process 200 provides for forming at least one forced-air pneumatic pathway formed therein to carry warmed air to a patient over whom the blanket 101 is disposed. For many application settings it can be beneficial to form a plurality of such forced-air pneumatic pathways Per the foregoing description this blanket 101 also includes a plurality of orifices 102 formed through at least one side thereof. At least some of these orifices 102 are coincident with the aforementioned forced-air pneumatic pathway(s) such that at least some warmed air that is introduced into the at least one forced-air pneumatic pathway will exit via those orifices 102 to thereby warm a patient over whom the blanket 101 is disposed.

Figure 3:
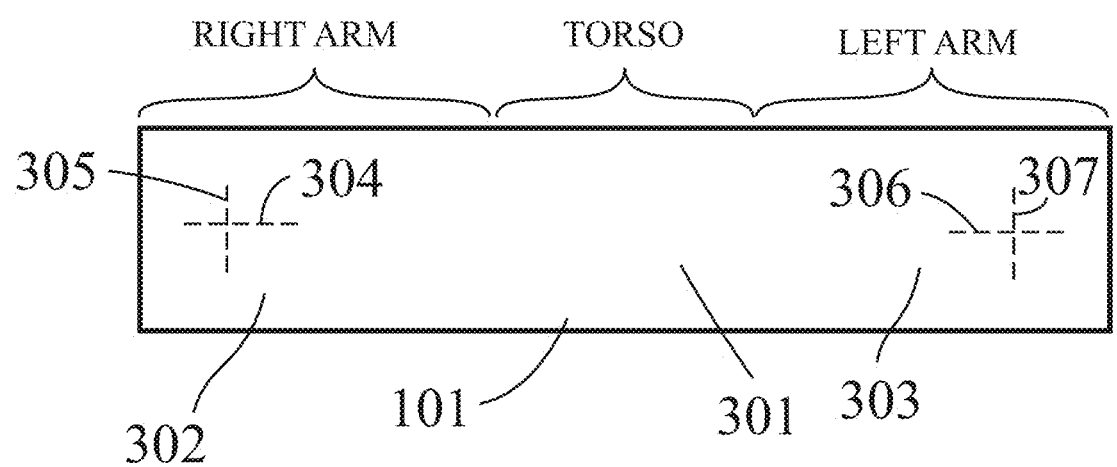
FIG. 3 comprises a top plan schematic view as configured in accordance with various embodiments of these teachings.

FIG. 3 presents one example in these regards. It will be understood that FIG. 3 presents a schematic representation to generally support this description. Accordingly, this example is not intended to specify any particular limitations as to the scope of these teachings except as may be specifically noted herein.

The blanket 101 shown in FIG. 3 is generally configured to cover a patient's upper torso and both arms (presuming that the patient's arms are extended laterally outward from the patient's torso). Accordingly, a middle portion 301 of the blanket 101 serves to cover at least a portion (such as an upper portion) of the patient's torso. A first portion 302 of the blanket 101 serves to cover the patient's right arm while a second portion 303, formed on the opposite side of the blanket 101 from the aforementioned first portion 302) serves to cover the patient's left arm.

Continuing to refer to both FIGS. 2 and 3, at block 203 this process 200 provides for forming a first tear line 304 in the first portion 302 of the blanket 101. By one approach the tear lines described herein comprise a line of perforations. These perforations can comprise a series of small holes that are disposed relatively close to one another such that the blanket material can be readily hand torn along the tear line without likely having the tear diverged laterally away from the tear line. The relative size and shape of each perforation can vary as desired and to accommodate, for example, the relative thickness and/or strength of the blanket material.

By another approach, in lieu of the foregoing or in combination therewith, such tear lines comprise a score line. A score line comprises a line formed by a shallow notch, channel, or other incision in the blanket material. As one illustrative example, plastic material can be removed to form such a notched line by use of a laser.

The foregoing examples are intended to serve an illustrative purpose and are not intended to constitute an exhaustive explanation of always of forming a tear line. Generally speaking, a tear line serves to guide the direction and extent of a hand-made tear such that the resulting tear tens to track and follow the tear line and to resist deviating from that tear line.

By one approach, and as shown in FIG. 3, this first tear line 304 is aligned at least substantially parallel to the first portion 302 of the blanket 101. In particular, this tear line 304 is aligned substantially in parallel with the longitudinal axis of that first portion 302. Also as illustrated, this tear line 304 is substantially centrally positioned with respect to the side edges of the corresponding first portion 302 of the blanket 101. These orientations will well serve the needs of many application settings. These teachings will also accommodate other approaches in these regards, however. By one approach, for example, this tear line 304 can be disposed at an acute angle with respect to the longitudinal axis of the first portion 302.

This tear line 304 is configured to facilitate forming a first hole in the blanket material to receive at least one of (1) a patient's appendages and (2) an operating room table's appendage board. In particular, a user can grip the blanket material (for example, proximal to and on either side of the tear line 304) to pull the blanket material laterally away from the tear line 304 on either side of the tear line 304 to thereby create such a hole.

As used herein, the word "appendage" will be understood to refer to a patient's arm or leg, where "arm" will be understood to refer to everything below the patient's shoulder including the patient's wrist and hand and where "leg" will be understood to refer to everything below the patient's hip including the patient's ankle and foot. The expression "operating room table's appendage board" will be understood to refer to arm boards as serve to specifically support a patient's arm when the patient's arm is disposed at least 30° outwardly of the patient's torso and leg boards as serve to specifically support a patient's leg when the patient's leg is disposed at least 20° outwardly of the patient's longitudinal axis.

With continued reference to FIGS. 2 and 3, at block 204 this process 200 provides for forming a second tear line 306 in the aforementioned second portion 303 of the blanket 101. By one approach this second tear line 306 is essentially a mirror image of the first tear line 304 and hence is similarly oriented and sized albeit on the opposite side of the blanket 101. So configured, this second tear line 306 again facilitates forming a hole (in this case a second hole) to receive at least one of another one of the patient's appendages and/or another one of the operating room table's appendage boards.

For many application settings the foregoing tear lines 304 and 306 may suffice. If desired, however, these teachings will readily accommodate forming additional tear lines. These additional tear lines can serve, for example, to particularly place and/or center a resultant hole. To illustrate, at optional blocks 205 and 206 this process 200 provides for forming a third tear line 305 in the blanket 101 that intersects the first tear line 304 and for forming a fourth tear line 307 in the blanket 101 that intersects the second tear line 306.

By one approach, these intersecting tear lines 305 and 307 are disposed at least substantially orthogonally to the first and second tear lines 304 and 306, respectively. By another approach, in lieu of the foregoing or in combination therewith, these intersecting tear lines 305 and 307 are disposed at least substantially parallel to one another.

Figure 4:
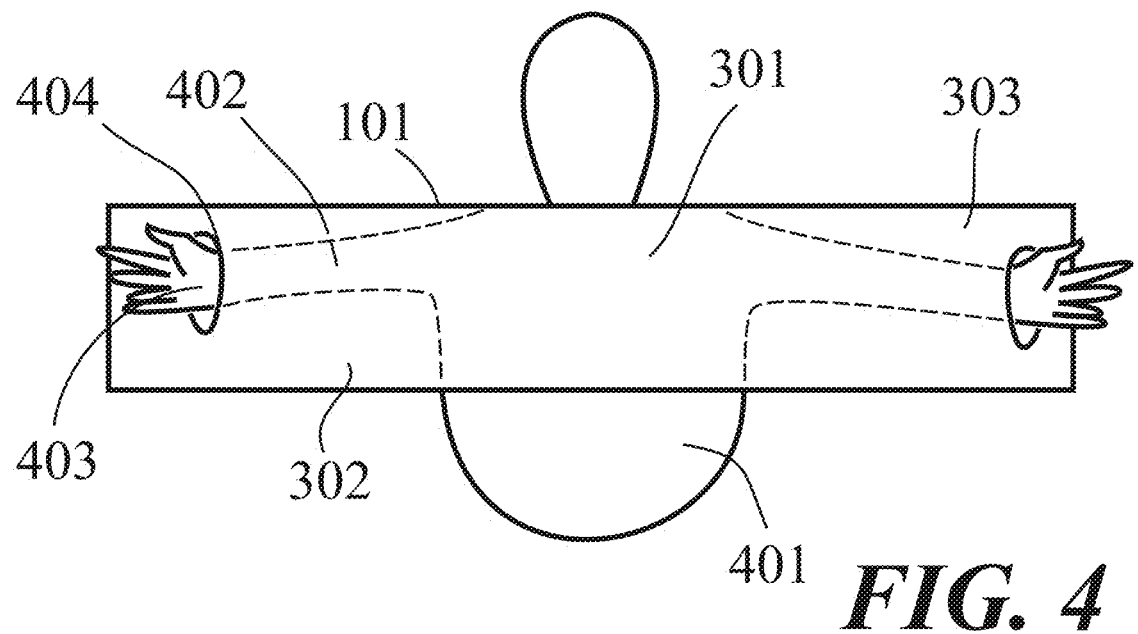
FIG. 4 comprises a top plan schematic view as configured in accordance with various embodiments of these teachings.

FIG. 4 illustrates such a blanket 101 disposed over a patient 401. In this example the aforementioned first portion 302 of the blanket 101 overlays, in part, the patient's right arm 402 and the aforementioned second portion 303 of the blanket 101 overlays, in part, the patient's left arm. In this illustrative example the aforementioned tear lines 304/305 and 306/307 have been utilized to form tears to thereby form corresponding holes. For example, the first and third tear lines 304 and 305 described above served to form a hole 404 that now accommodates the patient's right hand 403. A similar hole on the opposing side of the blanket 101 similarly accommodates the patient's left hand. So emplaced, the blanket 101 has been readily and easily secured in place with respect to the patient and will not tend to become dislodged during use.

Figure 5:
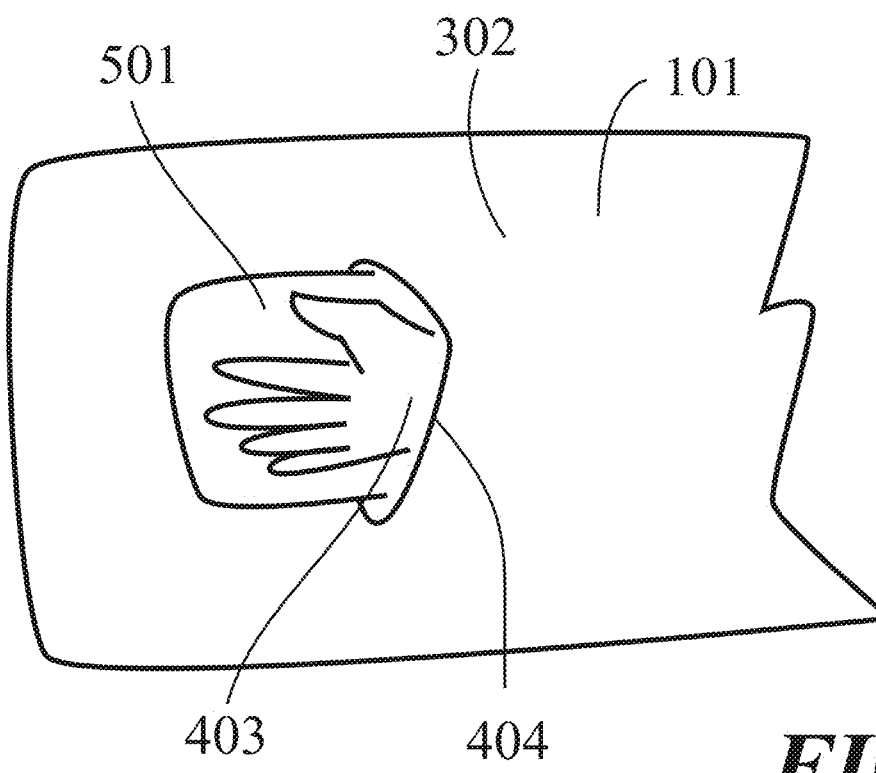
FIG. 5 comprises a top plan schematic detail view as configured in accordance with various embodiments of these teachings.

As noted above the holes formed by manipulation of the aforementioned tear lines can also serve to receive a portion of an operating room table's appendage board such as an arm board. FIG. 5 provides an illustrative example in this regard. In this example, both the patient's right hand 403 and the outer end of the corresponding arm board 501 that is supporting the patient's right arm are disposed through the aforementioned hole 404. The patient's left hand and its corresponding arm board can be similarly accommodated by the hole on the opposing side of the blanket 101 if desired.

Figure 6:
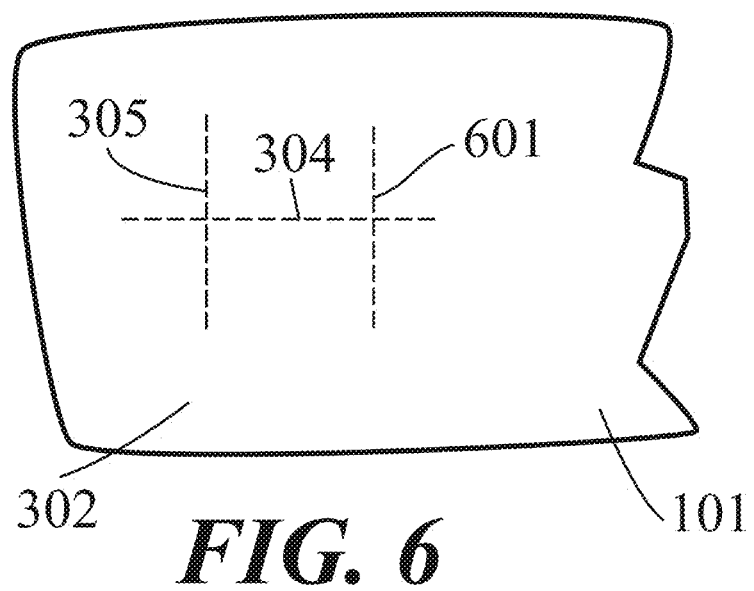
FIG. 6 comprises a top plan schematic detail view as configured in accordance with various embodiments of these teachings.

If desired, tear lines in addition to those described above can be further provided. FIG. 6 provides one illustrative example in these regards. In this example, the aforementioned first portion 302 of the blanket 101 includes not only the aforementioned first tear line 304 and the third tear line 305 that intersects the first tear line 304, but also another tear line 601 that also intersects the first tear line 304 and which is oriented at least substantially parallel, in this example, to the third tear line 305.

Figure 7:
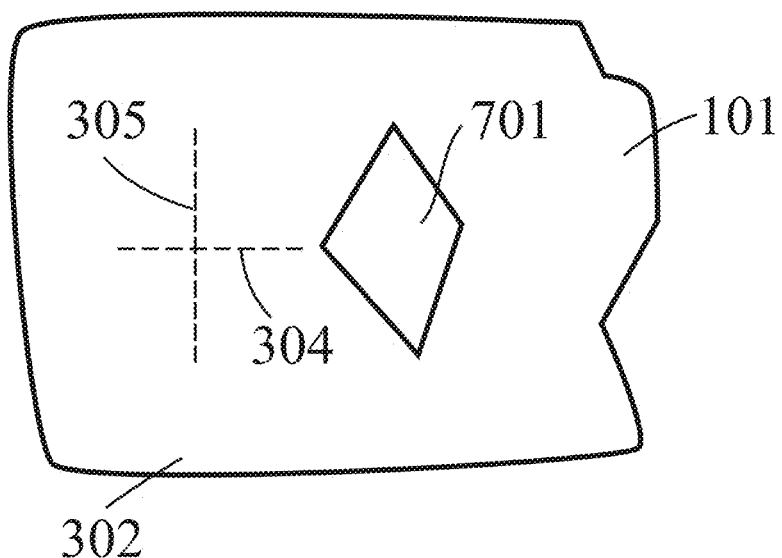
FIG. 7 comprises a top plan schematic detail view as configured in accordance with various embodiments of the invention.
Figure 8:
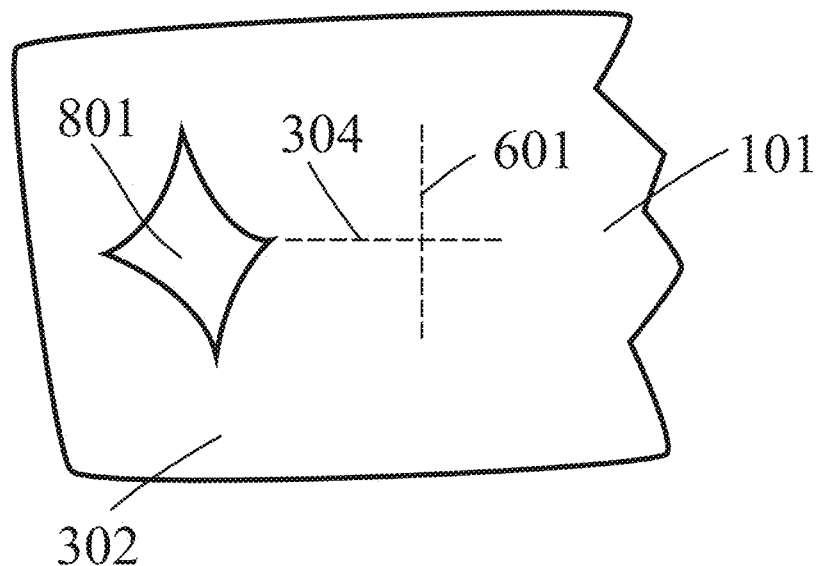
FIG. 8 comprises a top plan schematic detail view as configured in accordance with various embodiments of these teachings.

So configured, each tear line intersection can serve as a useful point at which to form the aforementioned hole. FIG. 7, for example, illustrates that the intersection of the first tear line 304 with the additional tear line 601 can form a hole 701 that is located relatively closer to the patient's torso and hence may better accommodate, for example, a patient having a shorter arm. FIG. 8, as another example, illustrates that the intersection of the first tear line 304 with the third tear line 305 can form a hole 801 that is located relatively further away from the patient's torso and hence may better accommodate a patient having a longer arm.

Figure 9:
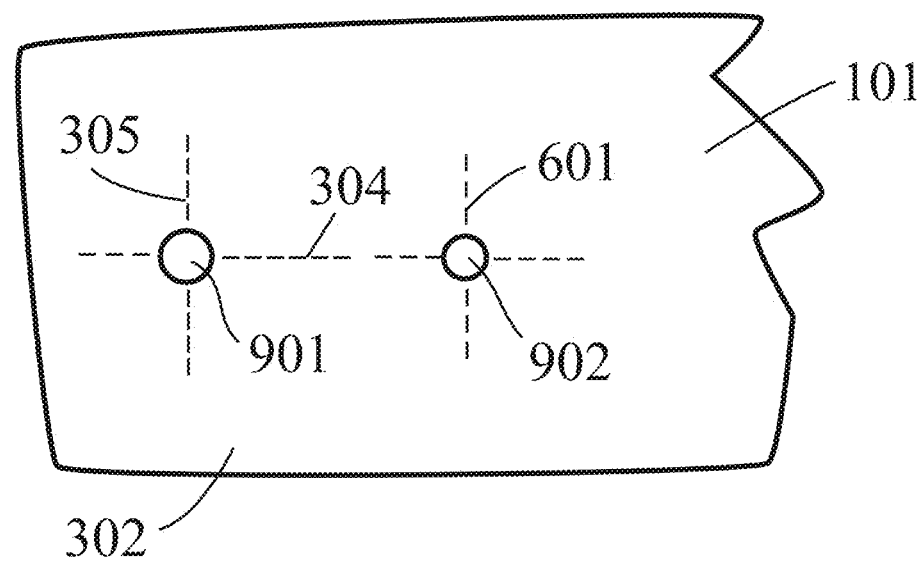
FIG. 9 comprises a top plan schematic detail view as configured in accordance with various embodiments of the invention.

If desired, these teachings will accommodate initially providing relatively larger holes through the blanket material in combination with one or more of the aforementioned tear lines. As one illustrative example in these regards, in FIG. 9 a first hole 901 is formed at the intersection of the first tear line 304 with the third tear line 305 and a second hole 902 is formed at the other tear line intersection. So configured, it may be easier for some users to begin a tear at a particular location that is useful in a particular application setting. Such holes 901 and 902 can be shaped and sized as desired. By one approach, and as but one illustrative example in these regards, such pre-formed and pre-placed holes 901 and 902 may have a diameter in the range of about 1 mm to about 10 mm.

Generally speaking, the aforementioned tear lines should typically not overlie or otherwise intersect any of the aforementioned forced-air pneumatic pathways. This is because forming a tear at an overlying tear line would form an additional opening through which warmed air could escape in a manner that may be less therapeutically beneficial to the patient.

Figure 10:
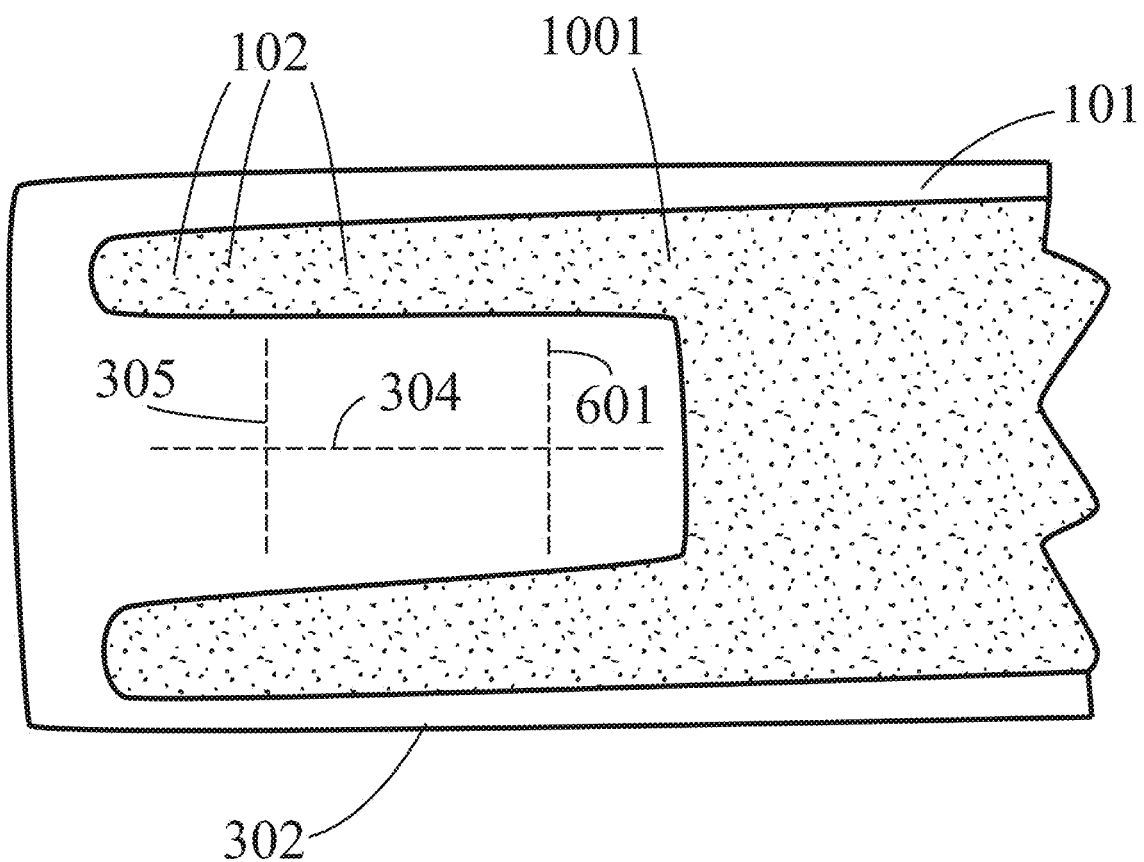
FIG. 10 comprises a bottom plan schematic detail view as configured in accordance with various embodiments of these teachings.

FIG. 10 provides one illustrative example in these regards. In this example a forced-air pneumatic pathway 1001 surrounds a grouping of tear lines 304, 305, and 601 on three sides, but none of the tear lines overlies or is otherwise commensurate with that forced-air pneumatic pathway 1001.

So configured, a blanket having one or more forced-air pneumatic pathways formed therethrough further includes tear lines formed in the blanket to facilitate forming holes to receive at least one of a patient's appendages and/or an operating room tables appendage board on either side of the blanket. Such holes are readily and easily formed by simple manipulation of the blanket material proximal such tear lines. The hole, in turn, can be located at a useful position in the blanket in an intuitive and reliable manner.

In many application settings such a blanket 101 can often be secured to the patient more easily and more quickly than by use of ties. Similarly, the blanket can be easily and quickly unsecured and removed from the patient upon conclusion of the corresponding medical procedure.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A personal patient warming apparatus comprising:
a blanket having a longitudinal axis and having at least one pneumatic pathway formed therein and a plurality of orifices formed through at least one side thereof such that at least some warmed air that is introduced into the at least one pneumatic pathway will exit via the plurality of orifices to thereby warm a patient over whom the blanket is disposed, the blanket further including:

a middle portion sized to cover the patient's upper torso;

a first portion disposed on a first lateral side of the middle portion to form a first end portion of the blanket, the first portion being sized to cover a first arm of the patient when the blanket is disposed over the patient and the first arm is extended laterally outward from the patient's torso;

a second portion disposed on a second lateral side of the middle portion that is opposite the first lateral side to form a second end portion of the blanket, the second portion sized to cover a second arm of the patient when the blanket is disposed over the patient and the second arm is extended laterally outward from the patient's torso;

and wherein both the first portion and the second portion each include at least one tear line located closer to a side edge of the blanket than to the middle portion that forms, when torn, an opening in the blanket through which at least one of the patient's hands and an operating room table arm board are disposed when disposing the blanket over the patient and wherein none of the tear lines extends all the way to an edge of the first portion or second portion;

such that the blanket covers the patient's upper torso and both arms excepting hands when the patient's arms are extended laterally outward from the patient's torso.

2. The personal patient warming apparatus of claim 1 wherein the blanket comprises a one-time-use disposable blanket.

3. The personal patient warming apparatus of claim 1 wherein the at least one tear line comprises at least one of a line of perforations and a score line.

4. The personal patient warming apparatus of claim 1 wherein the at least one tear line is aligned at least substantially parallel to the corresponding first and second portion of the blanket.

5. The personal patient warming apparatus of claim 4 wherein the at least one tear line is substantially centrally positioned with respect to side edges of the corresponding first and second portion of the blanket.

6. The personal patient warming apparatus of claim 1 wherein the at least one tear line comprises at least two tear lines that intersect one another.

7. The personal patient warming apparatus of claim 6 wherein the at least two tear lines are disposed at least substantially orthogonally to one another.

8. The personal patient warming apparatus of claim 6 wherein the at least two tear lines comprise at least three tear lines, wherein two of the at least three tear lines intersect another of the at least three tear lines.

9. The personal patient warming apparatus of claim 8 wherein the two of the at least three tear lines are disposed at least substantially parallel to one another.

* * * * *